United States Patent [19]
Alban et al.

[11] Patent Number: 5,318,774
[45] Date of Patent: Jun. 7, 1994

[54] COMPOSITION AND METHOD FOR IMPARTING AN ARTIFICIAL TAN TO HUMAN SKIN

[75] Inventors: Noelle C. Alban, Hamden; George E. Deckner, Trumbull, both of Conn.

[73] Assignee: Richardson-Vicks Inc., Shelton, Conn.

[21] Appl. No.: 843,044

[22] Filed: Feb. 28, 1992

[51] Int. Cl.$^5$ .................. A61K 7/021; A61K 7/42; A61K 7/44; A61K 9/10
[52] U.S. Cl. ............................... 424/59; 424/60; 424/63; 514/938
[58] Field of Search .................. 424/59, 60, 63

[56] References Cited

U.S. PATENT DOCUMENTS

| | | | |
|---|---|---|---|
| 3,177,120 | 4/1965 | Black et al. | 424/60 |
| 3,184,388 | 5/1965 | Kalopissis | 424/59 |
| 3,272,713 | 9/1966 | Runge | 424/59 |
| 3,920,808 | 11/1975 | Fusaro | 424/59 |
| 4,145,413 | 3/1979 | Usdin et al. | 424/63 |
| 4,159,318 | 6/1979 | Mausner et al. | 424/63 |
| 4,217,344 | 8/1980 | Vanlerberghe et al. | 424/60 |
| 4,419,343 | 12/1983 | Pauly | 424/59 |
| 4,832,943 | 5/1989 | Grollier et al. | 424/59 |
| 4,963,591 | 10/1990 | Fourman et al. | 514/944 |

FOREIGN PATENT DOCUMENTS

| | | | |
|---|---|---|---|
| 77-03895Y/03 | 12/1976 | Belgium | A61K 0/00 |
| 382619 | 8/1909 | European Pat. Off. | A61K 7/00 |
| 90-248499/33 | 8/1990 | European Pat. Off. | A61K 7/00 |
| 91-024247/04 | 1/1991 | European Pat. Off. | A61K 7/00 |
| 409690 | 1/1991 | European Pat. Off. | A61K 7/00 |
| 91-119499/17 | 4/1991 | European Pat. Off. | A61K 7/00 |
| 91-334476/46 | 4/1991 | European Pat. Off. | A61K 7/42 |
| 424282 | 4/1991 | European Pat. Off. | A61K 7/00 |
| 89-185978/26 | 6/1989 | France | A61K 7/42 |
| 90-099893/14 | 10/1989 | German Democratic Rep. | A61K 7/00 |
| 91-267058/36 | 8/1991 | PCT Int'l Appl. | A61K 7/02 |
| 83-825600/47 | 2/1983 | U.S.S.R. | A61K 7/00 |
| 2189457 | 10/1987 | United Kingdom | B01J 13/02 |

OTHER PUBLICATIONS

Handjani-Vila, R. M. et al. "Dispersions of Lamellar Phases of Non-Ionic Lipids in Cosmetic Products". Int'l J. of Cosmetic Science, 1, pp. 303-314 (1979).
CA98(16):132150g, Oct. 1, 1982, Spain.
CA72(20):103635b, Mar. 15, 1969, Czechoslovakia.

*Primary Examiner*—Dale R. Ore
*Attorney, Agent, or Firm*—Anthony D. Sabatelli; David K. Dabbiere

[57] ABSTRACT

The present invention relates to stabilized compositions, preferably in the form of oil-in-water emulsions, for imparting an artificial tan to human skin. The water phase of these compositions contains dihydroxyacetone and at least one alkyl hydroxyalkylcellulose or derivative thereof. The oil phase contains at least one fatty acid or fatty acid derivative. The weight ratio of fatty acid or fatty acid derivative to alkyl hydroxyalkylcellulose is most preferably from about 10:1 to about 5:1. In further embodiments, these emulsion compositions contain one or more sunscreens, and are also useful for protecting human skin from the harmful effects of sunlight and other sources of ultraviolet radiation.

20 Claims, No Drawings

COMPOSITION AND METHOD FOR IMPARTING AN ARTIFICIAL TAN TO HUMAN SKIN

TECHNICAL FIELD

The present invention relates to emulsion compositions having improved stability which are useful for imparting an artificial tan to human skin. These emulsions preferably comprise a water phase containing dihydroxyacetone and at least one alkyl hydroxyalkylcellulose or derivative thereof, and an oil phase comprising at least one fatty acid or fatty acid derivative. The weight ratio of fatty acid or fatty acid derivative to alkyl hydroxyalkylcellulose is most preferably from about 10:1 to about 5:1. In further embodiments, these emulsion compositions contain one or more sunscreens, and are also useful for protecting human skin from the harmful effects of sunlight and other sources of ultraviolet radiation. The present invention also relates to methods for preparing these compositions, methods for providing an artificial tan to human skin, and methods for protecting human skin from the harmful effects of ultraviolet radiation.

BACKGROUND OF THE INVENTION

It is generally known that dihydroxyacetone, when applied topically to human skin, will produce a tanned appearance, i.e. an artificial tan. U.S. Pat. No. 4,708,865, to Turner, issued Nov. 24, 1987 describes the use of hydro-alcoholic solutions of dihydroxyacetone for tanning the skin; U.S. Pat. No. 4,466,805, to Welters, issued Aug. 21, 1984 describes hair and skin coloring formulations containing dihydroxyacetone; and U.S. Pat. No. 2,949,403, to Andreadis et al., issued Aug. 16, 1960 describes artificial tanning formulations containing dihydroxyacetone in an oleaginous base. However, it is also known that emulsion products containing dihydroxyacetone have a short shelf life, tending to darken and develop disagreeable off-odors over time with a concomitant loss of emulsion integrity. Dihydroxyacetone is relatively sensitive to heat, light, moisture, and alkaline pH. Dihydroxyacetone can react with other ingredients in a formulation, especially with nitrogen-containing compounds, such as amines, amino acids, and the like. In fact, without being limited by theory, dihydroxyacetone is believed to provide an artificial tan to human skin by its reaction with the nitrogen containing proteins of the skin. See L. Goldman et al., "Investigative Studies with the Skin Coloring Agents Dihydroxyacetone and Glyoxal", *The Journal of Investigative Dermatology*, vol. 35, pp. 161–164 (1960); and E. Wittgenstein et al., "Reaction of Dihydroxyacetone (DHA) with Human Skin Callus and Amino Compounds", *The Journal of Investigative Dermatology*, vol. 36, pp. 283–286 (1961).

Currently available artificial tanning products have the disadvantage of not providing the desired control over color development of the tan. Artificial tans are often either too light or too dark, and tend to be too orange, uneven, or unnatural in appearance. Furthermore, artificial tans tend to take too long to develop, and once obtained, tend to fade too quickly and unevenly. Therefore, it would be highly desirable to provide dihydroxyacetone containing products which are chemically and physically stable, which are aesthetically pleasing, and which overcome these color development limitations.

A sun-tanned appearance is a symbol of a healthy, dynamic, and active life. Yet, the damaging effects of sunlight and artificial sources of ultraviolet radiation on the skin are well documented. Furthermore these effects are cumulative and potentially serious. These effects include erythema (i.e. sunburn), skin cancer, and premature aging of the skin. These adverse effects associated with exposure to ultraviolet radiation are more fully discussed in DeSimone, "Sunscreen and Suntan Products", *Handbook of Nonprescription Drugs*, 7th Ed., Chapter 26, pp. 499–511 (American Pharmaceutical Association, Washington, D.C.; 1982); Grove and Forbes, "A Method for Evaluating the Photoprotection Action of Sunscreen Agents Against UV-A Radiation", *International Journal of Cosmetic Science*, 4, pp. 15–24 (1982); and U.S. Pat. No. 4,387,089, DePolo, issued Jun. 7, 1983; the disclosures of all of which are incorporated herein by reference.

Sunscreens are the most common agents used for sun protection. However, sunscreens also have the disadvantage of preventing or greatly diminishing the cosmetically desirable tanning response. Thus, if an individual uses a sunscreen for protection from ultraviolet radiation, he or she is forced to forego a tanned appearance. Therefore, it would be highly desirable to provide protection from the harmful effects of ultraviolet radiation, and yet at the same time deliver a tanned appearance to the skin.

Furthermore, even if an individual is willing to accept the risks associated with exposure to ultraviolet radiation in order to obtain a tan, there are situations in which it may not be practical or even possible to do so because of time constraints, weather conditions, time of day, season of the year, geographic limitations, unavailability of an artificial ultraviolet radiation source, and the like. Therefore, it would be highly desirable to provide products that can deliver a tanned appearance whenever desired without the need for ultraviolet radiation.

Therefore, it would be highly desirable to provide a dihydroxyacetone containing emulsion for delivering both an artificial tan and also for providing protection from ultraviolet radiation. The combination of 3% dihydroxyacetone with 0.25% lawsone as a sunscreen active combination is described in the *Federal Register*, Vol. 43, No. 166, pp. 38206–38269, Aug. 25, 1978, this reference being incorporated herein by reference in its entirety. However, this combination is unsuitable for high SPF products. Furthermore, lawsone is a high melting bright yellow solid which is difficult to formulate and which is not readily available from suppliers in the United States. U.S. Pat. No. 3,177,120, to Black et al., issued Apr. 6, 1965 and U.S. Pat. No. 4,434,154, to McShane, issued Feb. 28, 1984 disclose dihydroxyacetone containing formulations which also incorporate a sunscreen. The '120 patent teaches compositions limited to the use of a single sunscreen not containing active amino groups (e.g., either homomenthyl salicylate or 2-ethoxyethyl p-methoxycinnamic acid); the '154 patent is limited to the use of octyl dimethyl PABA. However, homomenthyl salicylate is a very weak sunscreen unsuitable for use in products designed to deliver a high sun protection factor (i.e. SPF). Similarly, it is difficult to deliver high SPFs using either 2-ethoxyethyl p-methoxycinnamic acid or octyl dimethyl PABA, alone. Furthermore, due to growing consumer concerns over the use of PABA and PABA esters in sunscreen products, it would be preferable to develop dihydroxyacetone containing products which do not contain PABA and PABA derivatives. Therefore, the need exists for stabilized products which are effective for providing an artificial tan and which also provide adequate protection against ultraviolet radiation.

It is therefore an object of the present invention to provide emulsion compositions for imparting an artificial tan to human skin. Another object of the present invention is to provide emulsion compositions for imparting an artificial tan which exhibit a high degree of chemical and physical stability. A further object of the present invention is to provide stabilized emulsion compositions which are aesthetically appealing to consumers. A still further object of the present invention is to provide compositions for both imparting an artificial tan to human skin and also for protecting the skin from ultraviolet radiation. It is an even further object of the present invention is provide a method for artificially tanning human skin. It is another object of the present invention to provide a method for both artificially tanning human skin and for providing protection against ultraviolet radiation.

These and other objects of this invention will become apparent in light of the following disclosure.

SUMMARY OF THE INVENTION

The present invention relates to an artificial tanning composition having improved stability comprising:
a water phase and an oil phase
  (a) wherein said water phase comprises from about 0.1% to about 20% dihydroxyacetone and from about 0.1% to about 5% of at least one alkyl hydroxyalkylcellulose,
  (b) wherein said oil phase comprises from about 0.5% to about 20% of at least one fatty acid, fatty acid alcohol, fatty acid ester, or fatty acid ether, and
  wherein the weight ratio of said fatty acid or said alkyl hydroxyalkylcellulose is from about 35:1 to about 1:1, and said composition has a pH from about 2.5 to about 6.

All percentages and ratios used herein are by weight and all measurements are at 25° C., unless otherwise indicated.

DETAILED DESCRIPTION OF THE INVENTION

Emulsion Compositions

The compositions of the instant invention are in the form of emulsion compositions, preferably oil-in-water emulsions whereby the oil phase can contain typical oil-soluble components and the water phase can contain typical water-soluble materials. These types of emulsions are preferred because of their desirable aesthetic properties and their utility as vehicles for the dihydroxyacetone and the other essential and optional components of this invention. These emulsions can cover a broad range of consistencies including lotions, light creams, heavy creams, and the like.

To obtain an artificial tan using the emulsions of the instant invention, an effective amount of the emulsion is topically applied to human skin. By "effective" is meant an amount sufficient to provide an artificial tan when the composition is topically applied, but not so much as to cause any side effects or skin reactions. Quantities of emulsion which can be topically applied to provide an artificial tan are about, but not limited to, 2 mg/cm$^2$.

pH Requirements

The pH of a formulation is an important factor in determining the stability of the dihydroxyacetone. For example, it is well known that dihydroxyacetone rapidly degrades at extremes of alkaline pH. Suppliers of dihydroxyacetone suggest a preferred formulation pH range of between 4 and 6, and recommend the use of a buffer system to stabilize the pH value at about 5. See "Dihydroxyacetone for Cosmetics", E. Merck Technical Bulletin, 03-304 110, 319 897, 180 588, this reference being incoporated herein by reference in its entirety. However, the compositions of the instant invention preferably do not contain a buffer, because it has been determined that unbuffered formulations demonstrate improved chemical and physical stability compared to buffered formulations. The compositions of the instant invention preferably have a pH range from about 2.5 to about 7, more preferably from about 2.5 to about 6, even more preferably from about 3.5 to about 5, and most preferably from about 4 to about 4.75.

Dihydroxyacetone

An essential component of the water phase of the present compositions is dihydroxyacetone. Dihydroxyacetone, which is also known as DHA or 1,3-dihydroxy-2-propanone, is a white to off-white, crystalline powder having a characteristic sweet, cooling taste. The compound can exist as a mixture of monomers and dimers, with the dimer predominating. Heating or melting dimeric dihydroxyacetone converts the material into the monomeric form. The conversion of the dimer to the monomer also takes place in aqueous solution. See *The Merck Index*, Tenth Edition, entry 3167, p. 463 (1983), this reference being incorporated herein by reference in its entirety.

Without being limited by theory, it is believed that dihydroxyacetone reacts with the amino acids and amino groups of the skin keratin forming the brown colored compounds which provide an artificial tan. The process takes place in the outer layers of the epidermis. It is believed that the monomer is the active form responsible for this phenomenon. There is much evidence to suggest that the reaction of dihydroxyacetone with the components of the skin is similar to the Maillard Reaction. In this reaction, reducing sugars react with amino acids, proteins, and peptides to form various adducts which are ultimately converted into brown-colored compounds. See V. R. Usdin, Artificial Tanning Preparations, *Cosmetics and Toiletries*, vol. 91 pp. 29–32 (March 1976), this reference being incorporated herein by reference in its entirety. Dihydroxyacetone is commercially available from E. Merck (Darmstadt, Germany) and Gist-Brocades Food Ingredients, Inc. (King of Prussia, Pa.).

The dihydroxyacetone of the emulsion compositions of the instant invention is present from about 0.1% to about 20%, more preferably from about 2% to about 7%, and most preferably from about 3% to about 5%.

Alkyl Hydroxyalkylcellulose

An essential component of the water phase of the compositions of the present invention is an alkyl hydroxyalkylcellulose or derivative thereof. These materials are nonionic, water-soluble cellulose-based materials containing both a hydrophobic alkyl group and a shorter chain, hydrophilic hydroxylalkyl group. Without being limited by theory, it is believed that the hydrophobic alkyl chain provides a viscosity and rheological effect through intramolecular and intermolecular associations. Also, it is believed that the hydrophobic alkyl group can interact with other components of the formulation.

Preferred as the alkyl hydroxyalkylcellulose materials are those in which the hydrophobic alkyl group has an average of from about 8 to about 30 carbon atoms, and the hydroxyalkyl group has from about 1 to about 4 carbon atoms. More preferred are materials with the hydrophobic alkyl group having an average of from about 10 to about 20 carbon atoms, and the hydroxyalkyl group having from about 2 to about 3 carbon atoms. Even more preferred are materials with the hydrophobic alkyl group having from about 14 to about 18 carbon atoms, and the hydroxyalkyl group having from about 2 to about 3 carbon atoms. Most preferred is cetyl hydroxyethylcellulose, which is commercially available as Natrasol ® plus CS, Grade 330 (hydrophobically modified hydroxyethylcellulose) from Aqualon Company (Wilmington, Del.). Cetyl Hydroxyethylcellulose is as a white to off-white powder having a density of about 0.75 g/cm$^3$ and is readily soluble in water.

The alkyl hydroxyalkylcellulose of the instant invention is present from about 0.1% to about 5%, more preferably from about 0.1% to about 1%, and most preferably from about 0.4% to about 0.6%.

Fatty Acid or Fatty Acid Derivative

An essential component of the oil phase of the compositions of the present invention is a fatty acid or fatty acid derivative. By the term fatty acid is meant any organic carboxylic acid from natural or synthetic sources having from about 10 or more carbon atoms. By the term fatty acid derivative is meant a material derived from a fatty acid such as an alcohol (i.e. fatty acid alcohol), ester (i.e. fatty acid ester), ether (i.e. fatty acid ether), and the like. Examples of fatty acid alcohols include the corresponding alcohols of the fatty acids described herein. Examples of fatty acid esters include fatty acids esterified with short chain (i.e. C1–C8 straight or branched chain) alcohols; short chain (i.e. C1–C8 straight or branched chain) acids esterified with fatty acid alcohols; fatty acids esterified with fatty acid alcohols; mono-, di-, and triglycerides of fatty acids; and ethoxylated and propoxylated derivatives of any of these esters (i.e. fatty acid esters incorporating variable numbers of ethylene glycol or propylene glycol units). Examples of fatty acid ethers include fatty acid alcohol ethers of short chain alcohols (i.e. C1–C8 straight or branched chain alcohols), fatty acid alcohol ethers of fatty acid alcohols, and ethoxylated and propoxylated fatty acid alcohol ethers.

Fatty acids and fatty acid derivatives suitable for incorporation in the oil phase of the instant invention are described in CTFA International Cosmetic Ingredient Dictionary Fourth Edition, which is incorporated herein by reference.

Non-limiting examples of fatty acids useful in the compositions of the instant invention include stearic acid, lauric acid, myristic acid, oleic acid, linoleic acid, and the like. Non-limiting examples of fatty acid alcohols include cetyl alcohol, lauryl alcohol, stearyl alcohol, and the like. Non-limiting examples of fatty acid esters include glyceryl stearate, isopropyl myristate, myristyl myristate, cetyl myristate, tribehenin, and the like. Non-limiting examples of fatty acid ethers include PPG-15 stearyl ether, PPG-4 lauryl ether, PPG-10 cetyl ether, ceteareth-10, ceteareth-12, ceteareth-20, steareth-10, steareth-16, steareth-20, ceteth-10, and the like.

Preferred for use in the compositions of the instant invention are fatty acid or fatty acid derivatives selected from the group consisting of C10 to C30 fatty acids; C10 to C30 fatty acid alcohols; C10 to C30 ethoxylated and propoxylated fatty acid alcohols; esters of C10 to C30 fatty acids with C1 to C30 alcohols; ethoxylated and propoxylated esters of C10 to C30 fatty acids with C1 to C30 alcohols; C10 to C30 mono-, di-, and triglycerides; C10 to C30 fatty acid ethers; ethoxylated and propoxylated C10 to C30 fatty acid ethers; and mixtures thereof.

More preferred for use in the compositions of the instant invention are fatty acid or fatty acid derivatives selected from cetyl alcohol, stearyl alcohol, ceteareth-10, ceteareth-12, ceteareth-20, steareth-10, steareth-16, steareth-20, glyceryl stearate, PPG-15 stearyl ethyl, PPG-3 myristyl ether, PPG-10 cetyl ether, and mixtures thereof.

The total amount of fatty acid or fatty acid derivative of the instant invention is present from about 0.5% to about 20%, more preferably from about 1% to about 10%, and most preferably from about 4% to about 6%.

Weight Ratio of Fatty Acid or Fatty Acid Derivative to Alkyl Hydroxyalkylcellulose An important criticality of the compositions of the instant invention is that the fatty acid(s) or fatty acid derivative(s) and the alkyl hydroxyalkylcellulose derivative(s) are present in a proper weight ratio. Preferably, the weight ratio of the total amount of fatty acid or fatty acid derivative to alkyl hydroxyalkylcellulose should be from about 35:1 to about 1:1, more preferably from about 15:1 to about 2:1, and most preferably from about 10:1 to about 5:1.

Optional Components

Each of the water and oil phases of the emulsions can comprise a wide variety of optional components. Typical of such optional components are:

Sunscreens

A very highly preferred optional component useful in the instant invention is a sunscreening agent. A wide variety of one or more conventional sunscreening agents are suitable for use in the present invention. Segarin, et al., at Chapter VIII, pages 189 et seq., of Cosmetics Science and Technology, disclose numerous suitable agents. Specific suitable sunscreening agents include, but are not limited to, for example: Ethylhexyl p-methoxycinnamate (available as Parsol MCX from Givaudan Corporation and also known as octyl methoxycinnamate), p-Aminobenzoic acid, its salts and its derivatives (ethyl, isobutyl, glyceryl esters; p-dimethylaminobenzoic acid; 2-ethylhexyl N,N-dimethylaminobenzoate); p-Methoxycinnamic Acid Diethanolamine Salt (available as Bernel Hydro from Bernel Chemical Co.); Anthranilates (i.e., o-aminobenzoates; methyl, octyl, amyl, menthyl, phenyl, benzyl, phenylethyl, linalyl, terpinyl, and cyclohexenyl esters); Salicylates (octyl, amyl, phenyl, benzyl, menthyl, glyceryl, and dipropyleneglycol esters); Cinnamic acid derivatives (menthyl and benzyl esters, -phenyl cinnamonitrile; butyl cinnamoyl pyruvate); Dihydroxycinnamic acid derivatives (umbelliferone, methylumbelliferone, methylaceto-umbelliferone); Trihydroxycinnamic acid derivatives (esculetin, methylesculetin, daphnetin, and the glucosides, esculin and daphnin); Hydrocarbons (diphenylbutadiene, stilbene); Dibenzalacetone and benzalacetophenone; 2-Phenyl-benzimidazole-5-sulfonic acid and its salts; Naphtholsulfonates (sodium salts of 2-naphthol 3,6-disulfonic and of 2-naphthol-6,8-disulfonic acids); Dihydroxy-naphthoic acid and its salts; o- and p-Hydroxybiphenyldisulfonates; Coumarin derivatives (7-hydroxy, 7-methyl, 3-phenyl); Diazoles (2-acetyl-3-bromoindazole, phenyl benzoxazole, methyl naphthoxazole, various aryl benzothiazoles); Quinine salts (bisulfate, sulfate, chloride, oleate, and tannate); Quinoline derivatives (8-hydroxyquinoline salts, 2-phenylquinoline); Hydroxy- or methoxy-substituted benzophenones; Uric and vilouric acids; Tannic acid and its derivatives (e.g., hexaethylether); (Butyl carbityl) (6-propyl piperonyl) ether; Hydroquinone; Benzophenones (Oxybenzone, Sulisobenzone, Dioxybenzone, Benzoresorcinol, 2,2',4,4'-Tetrahydroxybenzophenone, 2,2'-Dihydroxy-4,4'-dimethoxybenzophenone, Octabenzone; 4-Isopropyldibenzoylmethane; Butylmethoxydibenzoylmethane; Octocrylene; 4-isopropyl-di-benzoylmethane; and camphor derivatives such as methyl benzylidene or benzylidene camphor; and mixtures thereof. Other sunscreens include the solid physical sunblocks such as titanium dioxide (micronized titanium dioxide, 0.03 microns), zinc oxide, silica, iron oxide and the like. Without being limited by theory, it is believed that these inorganic materials provide a sunscreening benefit through reflecting, scattering, and absorbing harmful UV, visible, and infrared radiation.

Preferred among these sunscreens are those selected from the group consisting of ethylhexyl p-methoxycinnamate, octocrylene, octyl salicylate, oxybenzone, titanium dioxide, and mixtures thereof.

Typically, a safe and photoprotectively effective amount of sunscreen(s) can be used in the artificial tanning emulsions of the present invention. By "safe and photoprotectively" is meant an amount sufficient to provide photoprotection when the composition is applied, but not so much as to cause any side effects or skin reactions. Generally, the sunscreen(s) can comprise from about 0.5% to about 20% of the composition. Exact amounts will vary depending upon the sunscreen chosen and the desired Sun Protection Factor (SPF). SPF is a commonly used measure of photoprotection of a sunscreen against erythema. See Federal Register, Vol. 43, No. 166, pp. 38206–38269, Aug. 25, 1978.

Other useful sunscreens are those disclosed in U.S. Pat. No. 4,937,370, to Sabatelli, issued Jun. 26, 1990; and U.S. Pat. No. 4,999,186, to Sabatelli et al., issued Mar. 12, 1991; these two references being incorporated by reference herein. The sunscreening agents disclosed therein have, in a single molecule, two distinct chromophore moieties which exhibit different ultra-violet radiation absorption spectra. One of the chromophore moieties absorbs predominantly in the UVB radiation range and the other absorbs strongly in the UVA radiation range.

These sunscreening agents provide higher efficacy, broader UV absorption, lower skin penetration and longer lasting efficacy relative to conventional sunscreens.

Preferred members of this class of sunscreening agents are 4-N,N-(2-ethylhexyl)methylaminobenzoic acid ester of 2,4-dihydroxybenzophenone; N,N-di-(2-ethylhexyl)-4-aminobenzoic acid ester with 4-hydroxydibenzoylmethane; 4-N,N(2-ethylhexyl) methylaminobenzoic acid ester with 4-hydroxydibenzoylmethane; 4-N,N-(2-ethylhexyl)methylaminobenzoic acid ester of 2-hydroxy-4-(2-hydroxyethoxy)benzophenone; 4-N,N-(2-ethylhexyl) methylaminobenzoic acid ester of 4-(2-hydroxyethoxy)dibenzoylmethane; N-N-di-(2-ethylhexyl)-4-aminobenzoic acid ester of 2-hydroxy-4-(2-hydroxyethoxy)benzophenone; and N,N-di-(2-ethylhexyl)4-aminobenzoic acid ester of 4-(2-hydroxyethoxy)dibenzoylmethane; and mixtures thereof.

Humectants/Moisturizers

The artifical tanning compositions of the instant invention can also contain one or more humectants/moisturizers. A variety of humectants/moisturizers can be employed and can be present at a level of from about 1% to about 30%, more preferably from about 2% to about 8% and most preferably from about 3% to about 5%. These materials include urea; guanidine; glycolic acid and glycolate salts (e.g. ammonium and quaternary alkyl ammonium); lactic acid and lactate salts (e.g. ammonium and quaternary alkyl ammonium); polyhydroxy alcohols such as sorbitol, glycerin, hexanetriol, propylene glycol, hexylene glycol and the like; polyethylene glycol; sugars and starches; sugar and starch derivatives (e.g. alkoxylated glucose); D-panthenol; hyaluronic acid; lactamide monoethanolamine; acetamide monoethanolamine; and mixtures thereof.

Preferred humectants/moisturizers for use in the compositions of the present invention are the $C_3$–$C_6$ diols and triols. Especially preferred is the triol, glycerin.

Carboxylic Acid Copolymer

Another optional component of the compositions of the present invention is a carboxylic acid copolymer (i.e. an acrylic acid copolymer). These copolymers consist essentially of a colloidally water-soluble polymer of acrylic acid crosslinked with a polyalkenyl polyether of a polyhydric alcohol, and optionally an acrylate ester or a polyfunctional vinylidene monomer.

Preferred copolymers useful in the present invention are polymers of a monomeric mixture containing 95.9 to 98.8 weight percent of an olefinically unsaturated carboxylic monomer selected from the group consisting of acrylic, methacrylic and ethacrylic acids; about 1 to about 3.5 weight percent of an acrylate ester of the formula:

wherein R is an alkyl radical containing 10 to 30 carbon atoms and $R^1$ is hydrogen, methyl or ethyl; and 0.1 to 0.6 weight percent of a polymerizable cross-linking polyalkenyl polyether of a polyhydric alcohol containing more than one alkenyl ether group per molecule wherein the parent polyhydric alcohol contains at least 3 carbon atoms and at least 3 hydroxyl groups.

Preferably, these polymers contain from about 96 to about 97.9 weight percent of acrylic acid and from about 2.5 to about 3.5 weight percent of acrylic esters wherein the alkyl group contains 12 to 22 carbon atoms, and $R^1$ is methyl, most preferably the acrylate ester is stearyl methacrylate. Preferably, the amount of cross-linking polyalkenyl polyether monomer is from about 0.2 to 0.4 weight percent. The preferred crosslinking polyalkenyl polyether monomers are allyl pentaerythritol, trimethylolpropane diallylether or allyl sucrose. These polymers are fully described in U.S. Pat. No. 4,509,949, to Huang et al., issued Apr. 5, 1985, this patent being incorporated herein by reference.

Other preferred copolymers useful in the present invention are the polymers which contain at least two monomeric ingredients, one being a monomeric olefinically-unsaturated carboxylic acid, and the other being a polyalkenyl, polyether of a polyhydric alcohol. Additional monomeric materials can be present in the monomeric mixture if desired, even in predominant proportion.

The first monomeric ingredient useful in the production of these carboxylic polymers are the olefinically-unsaturated carboxylic acids containing at least one activated carbon-to-carbon olefinic double bond, and at least one carboxyl group. The preferred carboxylic monomers are the acrylic acids having the general structure

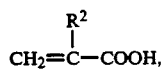

wherein $R^2$ is a substituent selected from the class consisting of hydrogen, halogen, and the cyanogen ($-C \equiv N$) groups, monovalent alkyl radicals, monovalent alkaryl radicals and monovalent cycloaliphatic radicals. Of this class, acrylic, methacrylic, and ethacrylic acid are most preferred. Another useful carboxylic monomer is maleic anhydride or the acid. The amount of acid used will be from about 95.5 to about 98.9 weight percent of the total monomers used. More preferably the range will be from about 96 to about 97.9 weight percent.

The second monomeric ingredient useful in the production of these carboxylic polymers are the polyalkenyl polyethers having more than one alkenyl ether grouping per molecule. The most useful possess alkenyl groups in which an olefinic double bond is present attached to a terminal methylene grouping, $CH_2=C<$.

The additional monomeric materials which can be present in the polymers include polyfunctional vinylidene monomers containing at least two terminal $CH_2<$ groups, including for example, butadiene, isoprene, divinyl benzene, divinyl naphthalene, allyl acrylates, and the like. These polymers are fully described in U.S. Pat. No. 2,798,053, to Brown, H. P., issued Jul. 2, 1957, this patent being incorporated herein by reference.

Examples of carboxylic acid copolymers useful in the present invention include Carbomer 934, Carbomer 941, Carbomer 950, Carbomer 951, Carbomer 954, Carbomer 980, Carbomer 981, Carbomer 1342, and Acrylates/$C_{10-30}$ Alkyl Acrylate Cross Polymers (available as Carbopol® 934, Carbopol® 941, Carbopol® 950, Carbopol® 951, Carbopol® 954, Carbopol® 980, Carbopol® 981, Carbopol® 1342, and the Pemulen Series, respectively, from B.F. Goodrich).

Other carboxylic acid copolymers useful in the present invention include sodium salts of acrylic acid/acrylamide copolymers sold by the Hoechst Celanese Corporation under the trademark of Hostaceren PN73. Also included are the hydrogel polymers sold by Lipo Chemicals Inc. under the trademark of HYPAN hydrogels. These hydrogels consist of crystalline plicks of nitrites on a C—C backbone with various other pendant groups such as carboxyls, amides, and amidines. An example would include HYPAN SA100 H, a polymer powder available from Lipo Chemical.

The carboxylic acid copolymers can be used individually or as a mixture of two or more polymers and comprise from about 0.025% to about 2.00%, preferably from about 0.1% to about 1.50% and most preferably from about 0.40% to about 1.25% of the compositions of the present invention.

Emollients

The compositions of the present invention can also optionally comprise at least one emollient. Examples of suitable emollients include, but are not limited to, volatile and non-volatile silicone oils, highly branched hydrocarbons, and non-polar carboxylic acid and alcohol esters, and mixtures thereof. Emollients useful in the instant invention are further described in U.S. Pat. No. 4,919,934, to Deckner et al., issued Apr. 24, 1990, which is incorporated herein by reference in its entirety.

The emollients can typically comprise in total from about 1% to about 50%, preferably from about 1% to about 25%, and more preferably from about 1% to about 10% by weight of the compositions of the present invention.

Emulsifiers

The compositions of the present invention can optionally comprise additional emulsifiers and surfactants. Suitable emulsifiers can include, but are not limited to, polyethylene glycol 20 sorbitan monolaurate (Polysorbate 20), polyethylene glycol 5 soya sterol, polyethylene glycol 100 stearate, polyethylene glycol 20 stearyl ether, Polysorbate 80, cetyl phosphate, potassium cetyl phosphate, ethanolamine cetyl phosphate, diethanolamine cetyl phosphate, triethanolamine cetyl phosphate, and mixtures thereof. Examples of a broad variety of additional emulsifiers and surfactants useful herein are described in McCutcheon's, *Detergents and Emulsifiers*, North American Edition (1986), published by Allured Publishing Corporation, which is incorporated herein by reference in its entirety.

Vitamins

Various vitamins can also be included in the compositions of the present invention. Non-limiting examples include Vitamin A and derivatives thereof, ascorbic acid, Vitamin B complexes and derivatives thereof such as panthothenic acid, biotin, Vitamin D, Vitamin E and derivatives thereof such as tocopheryl acetate, and mixtures thereof.

Other Optional Components

A variety of additional ingredients can be incorporated into the emulsion compositions of the present invention. Non-limiting examples of these additional ingredients include various polymers for aiding the film-forming properties and substantivity of the formulation (e.g., PVP/eicosene copolymer available as Ganex® V-220 from GAF Corp); gums, resins, and thickeners; preservatives for maintaining the antimicrobial integrity of the compositions; antioxidants; chelators and sequestrants; and agents suitable for aesthetic purposes such as fragrances, pigments, opacifiers, and colorings.

EXAMPLES

The following examples further describe and demonstrate embodiments within the scope of the present invention. The examples are given solely for the purpose of illustration and are not to be construed as limitations of the present invention, as many variations thereof are possible without departing from the spirit and scope of the invention.

Ingredients are identified by chemical or CTFA name.

EXAMPLE I

Artificial Tanning Lotion

An oil-in-water emulsion is prepared by combining the following components utilizing conventional mixing techniques.

| Ingredients | % Weight |
|---|---|
| Phase A | |
| Water qs | 100 |
| Cetyl Hydroxethylcellulose[1] | 0.50 |
| Disodium EDTA | 0.030 |
| Phase B | |
| PPG-15 Stearyl Ether | 11.0 |
| Dimethicone & Trimethylsiloxysilicate[2] | 2.00 |
| Dimethicone | 1.00 |
| Glyceryl Stearate | 2.60 |
| PVP/Eicosene Copolymer | 0.80 |
| Cetyl Alcohol | 0.75 |
| Stearyl Alcohol | 0.50 |
| Ceteareth-12 | 0.50 |
| Ceteareth-20 | 0.50 |
| Phase C | |
| Water | 2.00 |
| Butylene Glycol | 2.00 |
| DMDM Hydantoin (and) | 0.20 |
| Iodopropynyl Butylcarbamate | |
| Phase D | |
| Water | 6.00 |
| Dihydroxyacetone | 3.00 |
| Phase E | |
| Fragrance | 1.00 |

[1] Available as Natrasol ® CS Plus 330 Grade from Aqualon.
[2] Available as Dow Corning 593 Fluid.

In a suitable vessel the Phase A ingredients are dispersed in the water and heated to 75°-85° C. In a separate vessel the Phase B ingredients are combined and heated to 85°-90° C. until melted and this mixture is then added to Phase A to form the emulsion. The emulsion is cooled to 40°-45° C. with continued mixing. In a separate vessel, the Phase C ingredients are combined and the resulting solution is mixed into the emulsion. In a separate vessel, the dihydroxyacetone is dissolved in water to form Phase D, and the resulting solution is mixed into the emulsion. Finally, the fragrance, Phase E, is added to the emulsion with mixing, which is then cooled to 30°-35° C., and then to room temperature.

This emulsion has improved stability and is useful for topical application to the skin to provide an artificial tan.

EXAMPLE II

High SPF Artificial Tanning Lotion

An oil-in-water emulsion is prepared by combining the following components utilizing conventional mixing techniques.

| Ingredients | % Weight |
|---|---|
| Phase A | |
| Water qs | 100 |
| Cetyl Hydroxethylcellulose[1] | 0.50 |
| Disodium EDTA | 0.030 |
| Phase B | |
| Octyl Methoxycinnamate | 7.50 |
| Oxybenzone | 2.50 |
| Octocrylene | 1.00 |
| Dimethicone & Trimethylsiloxysilicate[2] | 2.00 |
| Dimethicone | 1.00 |
| Glyceryl Stearate | 2.60 |
| PVP/Eicosene Copolymer | 0.80 |
| Cetyl Alcohol | 0.75 |
| Stearyl Alcohol | 0.50 |
| Ceteareth-12 | 0.50 |
| Ceteareth-20 | 0.50 |
| Phase C | |
| Water | 2.00 |
| Butylene Glycol | 2.00 |
| DMDM Hydantoin (and) | 0.20 |
| Iodopropynyl Butylcarbamate | |
| Phase D | |
| Water | 6.00 |
| Dihydroxyacetone | 3.00 |
| Phase E | |
| Fragrance | 1.00 |

[1] Available as Natrasol ® CS Plus 330 Grade from Aqualon.
[2] Available as Dow Corning 593 Fluid.

An emulsion is prepared from the above ingredients employing the method described in Example I.

This emulsion has improved stability and is useful for topical application to the skin to provide an artificial tan and to provide protection of the skin from the harmful effects of ultraviolet radiation.

EXAMPLE III

Low SPF Artificial Tanning Lotion

An oil-in-water emulsion is prepared by combining the following components utilizing conventional mixing techniques.

| Ingredients | % Weight |
|---|---|
| Phase A | |
| Water qs | 100 |
| Cetyl Hydroxethylcellulose[1] | 0.50 |
| Disodium EDTA | 0.030 |
| Phase B | |
| Octyl Methoxycinnamate | 3.00 |
| Octyl Salicylate | 0.50 |
| PPG-15 Stearyl Ether | 4.00 |
| Dimethicone & Trimethylsiloxysilicate | 2.00 |
| Dimethicone | 1.00 |
| Glyceryl Stearate | 2.60 |
| PVP/Eicosene Copolymer | 0.80 |
| Cetyl Alcohol | 0.75 |
| Stearyl Alcohol | 0.50 |
| Ceteareth-12 | 0.50 |
| Ceteareth-20 | 0.50 |
| Phase C | |
| Water | 2.00 |
| Butylene Glycol | 2.00 |
| DMDM Hydantoin (and) | 0.20 |
| Iodopropynyl Butylcarbamate | |
| Phase D | |
| Water | 6.00 |
| Dihydroxyacetone | 3.00 |
| Phase E | |
| Fragrance | 1.00 |

[1] Available as Natrasol ® CS Plus 330 Grade from Aqualon.
[2] Available as Dow Corning 593 Fluid.

An emulsion is prepared from the above ingredients employing the method described in Example I.

This emulsion has improved stability and is useful for topical application to the skin to provide an artificial tan and to provide protection of the skin from the harmful effects of ultraviolet radiation.

EXAMPLE IV

High SPF Artificial Tanning Lotion With Glycerin

An oil-in-water emulsion is prepared by combining the following components utilizing conventional mixing techniques.

| Ingredients | % Weight |
| --- | --- |
| Phase A | |
| Water qs | 100 |
| Glycerin | 3.00 |
| Cetyl Hydroxethylcellulose[1] | 0.50 |
| Disodium EDTA | 0.030 |
| Phase B | |
| Octyl Methoxycinnamate | 7.50 |
| Oxybenzone | 2.50 |
| Octocrylene | 1.00 |
| Dimethicone & Trimethylsiloxysilicate[2] | 2.00 |
| Dimethicone | 1.00 |
| Glyceryl Stearate | 2.60 |
| PVP/Eicosene Copolymer | 0.80 |
| Cetyl Alcohol | 0.75 |
| Stearyl Alcohol | 0.50 |
| Ceteareth-12 | 0.50 |
| Ceteareth-20 | 0.50 |
| Phase C | |
| Water | 2.00 |
| Butylene Glycol | 2.00 |
| DMDM Hydantoin (and) Iodopropynyl Butylcarbamate | 0.20 |
| Phase D | |
| Water | 6.00 |
| Dihydroxyacetone | 3.00 |
| Phase E | |
| Fragrance | 1.00 |

[1]Available as Natrasol ® CS Plus 330 Grade from Aqualon.
[2]Available as Dow Corning 593 Fluid.

An emulsion is prepared from the above ingredients employing the method described in Example I.

This emulsion has improved stability and is useful for topical application to the skin to provide an artificial tan and to provide protection of the skin from the harmful effects of ultraviolet radiation.

What is claimed is:

1. An artificial tanning composition having improved stability comprising:
a water phase and an oil phase
   (a) wherein said water phase comprises from about 0.1% to about 20% dihydroxyacetone and from about 0.1% to about 5% of at least one alkyl hydroxyalkylcellulose,
   (b) wherein said oil phase comprises from about 0.5% to about 20% of at least one fatty acid, fatty acid alcohol, fatty acid ester, or fatty acid ether, and
   wherein the weight ratio of said fatty acid, fatty acid alcohol, fatty acid ester, or fatty acid ether to said alkyl hydroxyalkylcellulose is from about 35:1 to about 1:1, and said composition has a pH from about 2.5 to about 6.

2. The composition according to claim 1 wherein said weight ratio is from about 15:1 to about 2:1.

3. The composition according to claim 2 wherein said weight ratio is from about 10:1 to about 5:1.

4. The composition according to claim 3 wherein said composition has a pH from about 3.5 to about 5.

5. The composition according to claim 4 wherein said composition has a pH from about 4 to about 4.75.

6. The composition according to claim 5 wherein said dihydroxyacetone comprises from about 2% to about 7%.

7. The composition according to claim 6 wherein said dihydroxyacetone comprises from about 3% to about 5%.

8. The composition according to claim 7 wherein said alkyl hydroxyalkylcellulose comprises from about 0.4% to about 0.6%.

9. The composition according to claim 8 wherein said fatty acid, fatty acid alcohol, fatty acid ester, or fatty acid ether comprises from about 4% to about 6%.

10. The composition according to claim 7 wherein said alkyl hydroxyalkylcellulose is such that the alkyl group contains from about 8 to about 30 carbon atoms and the hydroxyalkyl group contains from about 1 to about 4 carbon atoms.

11. The composition according to claim 10 wherein said alkyl hydroxyalkylcellulose is such that the alkyl group contains from about 14 to about 18 carbon atoms and the hydroxyalkyl group contains from about 2 to about 3 carbon atoms.

12. The composition according to claim 11 wherein said alkyl hydroxyalkylcellulose is cetyl hydroxyethylcellulose.

13. The composition according to claim 12 wherein said fatty acid, fatty acid alcohol, fatty acid ester, or fatty acid ether is selected from the group consisting of C10 to C30 fatty acids; C10 to C30 fatty acid alcohols; C10 to C30 ethoxylated and propoxylated fatty acid alcohols; esters of C10 to C30 fatty acids with C1 to C30 alcohols; ethoxylated and propoxylated esters of C10 to C30 fatty acids with C1 to C30 alcohols; C10 to C30 mono-, di-, and triglycerides; C10 to C30 fatty acid ethers; ethoxylated and propoxylated C10 to C30 fatty acid ethers; and mixtures thereof.

14. The composition according to claim 13 wherein said fatty acid, fatty acid alcohol, fatty acid ester, or fatty acid ether is selected from cetyl alcohol, stearyl alcohol, ceteareth-10, ceteareth-12, ceteareth-20, steareth-10, steareth-16, steareth-20, glyceryl stearate, PPG-15 stearyl ether, PPG-3 myristyl ether, PPG-10 cetyl ether, and mixtures thereof.

15. The composition according to claim 14 wherein said composition further comprises from about 0.5% to about 20% of at least one sunscreening agent selected from the group consisting of ethylhexyl p-methoxycinnamate, octyl salicylate, octocrylene, oxybenzone, 2-ethylhexyl N,N-dimethylaminobenzoate, 2-Phenyl-benzimidazole-5-sulfonic acid, 4-N,N-(2-ethylhexyl)methylaminobenzoic acid ester of 2,4-dihydroxybenzophenone, N,N-di-(2-ethylhexyl)-4-aminobenzoic acid ester with 4-hydroxydibenzoylmethane, 4-N,N(2-ethylhexyl) methylaminobenzoic acid ester with 4-hydroxydibenzoylmethane, 4-N,N-(2-ethylhexyl)methylaminobenzoic acid ester of 2-hydroxy-4-(2-hydroxyethoxy)benzophenone, 4-N,N-(2-ethylhexyl) methylaminobenzoic acid ester of 4-(2-hydroxyethoxy)dibenzoylmethane, N-N-di-(2-ethylhexyl)-4-aminobenzoic acid ester of 2-hydroxy-4-(2-hydroxyethoxy)benzophenone, N,N-di-(2-ethylhexyl)4-aminobenzoic acid ester of 4-(2-hydroxyethoxy)dibenzoylmethane, titanium dioxide, zinc oxide, and mixtures thereof.

16. The composition according to claim 15 wherein said sunscreening agent is selected from the group consisting of ethylhexyl p-methoxycinnamate, octocrylene, octyl salicylate, oxybenzone, titanium dioxide, and mixtures thereof.

17. A method for providing an artificial tan to human skin, said method comprising topically applying to the skin of the human an effective amount of a composition according to claim 1.

18. A method for providing an artificial tan to human skin, said method comprising topically applying to the skin of the human an effective amount of a composition according to claim 14.

19. A method for providing both an artificial tan to human skin and protecting human skin from the effects of ultraviolet radiation, said method comprising topically applying to the skin of the human an effective amount of a composition according to claim 15.

20. A method for providing both an artificial tan to human skin and protecting human skin from the effects of ultraviolet radiation, said method comprising topically applying to the skin of the human an effective amount of a composition according to claim 16.

* * * * *